United States Patent
Suzuki et al.

(10) Patent No.: US 10,769,201 B2
(45) Date of Patent: Sep. 8, 2020

(54) IMAGE MANAGEMENT DEVICE, IMAGE DISPLAY SYSTEM, AND IMAGE DISPLAY METHOD

(71) Applicant: Konica Minolta, Inc., Chiyoda-ku, Tokyo (JP)

(72) Inventors: Kenichirou Suzuki, Mitaka (JP); Takao Shiibashi, Hachioji (JP); Akira Kurahashi, Hachioji (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 160 days.

(21) Appl. No.: 15/660,262

(22) Filed: Jul. 26, 2017

(65) Prior Publication Data
US 2018/0032547 A1 Feb. 1, 2018

(30) Foreign Application Priority Data
Jul. 26, 2016 (JP) ................... 2016-145894

(51) Int. Cl.
*G06F 16/54* (2019.01)
*G06F 16/58* (2019.01)
(Continued)

(52) U.S. Cl.
CPC ......... *G06F 16/5866* (2019.01); *G16H 30/20* (2018.01); *H04N 1/00129* (2013.01); *G06F 16/54* (2019.01)

(58) Field of Classification Search
CPC ........ G16H 30/00; G16H 30/20; G16H 30/40; G06F 19/321; G06F 16/5866; G06F 16/54; G06F 16/587; H04N 1/00129
See application file for complete search history.

(56) References Cited

U.S. PATENT DOCUMENTS

2003/0156745 A1* 8/2003 Saito ............... G06F 19/321
382/128
2003/0187998 A1* 10/2003 Petit ............... H04L 63/102
709/229
(Continued)

FOREIGN PATENT DOCUMENTS

JP 2000285131 A 10/2000
JP 2005218847 A 8/2005
(Continued)

OTHER PUBLICATIONS

JPO Notice of Reasons for Refusal for corresponding JP2016-145894; dated Jun. 9, 2020.

*Primary Examiner* — Jorge A Casanova
(74) *Attorney, Agent, or Firm* — Cantor Colburn LLP (57) ABSTRACT

An image management device that is communicably connected to a client terminal and a plurality of image storage devices, includes: a storage that stores identification information of image data with the identification information associated with an image storage device in which the image data is stored; a hardware processor that identifies an image storage device that stores image data specified by an image-data transmission request received from the client terminal based on the identification information of the image data stored in the storage, and instructs the identified image storage device to subject the image data specified by the transmission request to image processing; and a communicator that receives, from the identified image storage device, processed image data that has been subjected to the image processing, and transmits the processed image data to the client terminal.

7 Claims, 7 Drawing Sheets

(51) Int. Cl.
*H04N 1/00* (2006.01)
*G16H 30/20* (2018.01)

(56) References Cited

U.S. PATENT DOCUMENTS

| | | | | |
|---|---|---|---|---|
| 2005/0254729 | A1* | 11/2005 | Saito | G06F 19/321 |
| | | | | 382/305 |
| 2006/0010013 | A1* | 1/2006 | Yamatake | G06F 19/321 |
| | | | | 705/2 |
| 2006/0241968 | A1* | 10/2006 | Hollebeek | G06F 9/5011 |
| | | | | 705/2 |
| 2007/0036268 | A1* | 2/2007 | Matsuno | A61B 6/00 |
| | | | | 378/98.2 |
| 2007/0107033 | A1* | 5/2007 | Ho | G06F 11/1451 |
| | | | | 725/115 |
| 2008/0005059 | A1* | 1/2008 | Colang | G06F 19/321 |
| 2009/0132636 | A1* | 5/2009 | Natanzon | G06F 19/321 |
| | | | | 709/201 |
| 2010/0054566 | A1* | 3/2010 | Toda | G06F 19/321 |
| | | | | 382/131 |
| 2010/0246981 | A1* | 9/2010 | Hu | G06F 19/321 |
| | | | | 382/232 |
| 2011/0311021 | A1* | 12/2011 | Tsukagoshi | A61B 6/461 |
| | | | | 378/19 |
| 2014/0114683 | A1* | 4/2014 | Natanzon | G06F 19/321 |
| | | | | 705/2 |
| 2014/0115020 | A1* | 4/2014 | Colaco | G06F 16/182 |
| | | | | 707/827 |
| 2015/0078682 | A1* | 3/2015 | Dutta | G06F 16/58 |
| | | | | 382/305 |
| 2015/0092090 | A1* | 4/2015 | Miura | H04N 9/646 |
| | | | | 348/242 |
| 2015/0150086 | A1* | 5/2015 | Clark | G16H 10/60 |
| | | | | 726/3 |
| 2016/0092446 | A1* | 3/2016 | Nye | G06T 3/00 |
| | | | | 705/3 |
| 2016/0217339 | A1* | 7/2016 | Zhao | A61B 90/37 |

FOREIGN PATENT DOCUMENTS

| | | |
|---|---|---|
| JP | 2009258777 A | 11/2009 |
| JP | 2012100691 A | 5/2012 |
| JP | 2012194825 A | 10/2012 |
| JP | 5855807 B2 | 2/2016 |

\* cited by examiner

| IMAGE UID | INSPECTION UID | SeriesUID | Date | Path | Flag |
|---|---|---|---|---|---|
| 0001 | x.x.xxxxx.xx | x.x.xxxxx.xx | 2015/1/1 | #2 | No |
| 0002 | x.x.xxxxx.xx | x.x.xxxxx.xx | 2015/1/2 | #3 | No |
| 0003 | x.x.xxxxx.xx | x.x.xxxxx.xx | 2015/6/6 | #1 | No |
| 0004 | x.x.xxxxx.xx | x.x.xxxxx.xx | 2016/6/7 | #3 | Yes |

| IMAGE UID | INSPECTION UID | SeriesUID | Date | Path | Flag |
|---|---|---|---|---|---|
| 0001 | x.x.xxxxx.xx | x.x.xxxxx.xx | 2015/1/1 | #2 | No |
| 0002 | x.x.xxxxx.xx | x.x.xxxxx.xx | 2015/1/2 | #3 | No |

| IMAGE UID | INSPECTION UID | SeriesUID | Date | Path | Flag |
|---|---|---|---|---|---|
| 0001 | x.x.xxxxx.xx | x.x.xxxxx.xx | 2015/1/1 | #2 | No |
| 0002 | x.x.xxxxx.xx | x.x.xxxxx.xx | 2015/1/2 | #3 | No |
| 0003 | x.x.xxxxx.xx | x.x.xxxxx.xx | 2015/6/6 | #1 | Yes |

| IMAGE UID | INSPECTION UID | SeriesUID | Date | Path | Flag |
|---|---|---|---|---|---|
| 0001 | x.x.xxxxx.xx | x.x.xxxxx.xx | 2015/1/1 | #2 | No |
| 0002 | x.x.xxxxx.xx | x.x.xxxxx.xx | 2015/1/2 | #3 | No |
| 0003 | x.x.xxxxx.xx | x.x.xxxxx.xx | 2015/6/6 | #1 | No |

US 10,769,201 B2

IMAGE MANAGEMENT DEVICE, IMAGE DISPLAY SYSTEM, AND IMAGE DISPLAY METHOD

CROSS-REFERENCE TO RELATED APPLICATIONS

The present invention claims priority under 35 U.S.C. § 119 to Japanese Patent Application No. 2016-145894, filed on Jul. 26, 2016, the entire contents of which are incorporated herein by reference.

BACKGROUND

Technological Field

The present invention relates to an image management device, an image display system, and an image display method.

Description of the Related Art

In a hospital, medical information including patient information, inspection information and medical images is managed by an image management device, and medical information is registered and browsed by accessing the image management device from a client terminal that is data-communicably connected to the image management device.

Conventionally, an image management device is composed of a main server and a plurality of subservers so as to reduce a load of the device.

For example, JP 5855807 B2 proposes a configuration of an image management server that is connected to a plurality of client terminals and a subserver, and that subjects a medical image read from a medical image storage device to image processing, wherein a load of the subserver and a load of an own device are monitored, and when an image processing request is received from a client terminal, a server, the load of which is lower than the other server, is instructed to execute the image processing.

However, in JP 5855807 B2, since a medical image is transmitted to a server, the load of which is lower, the time taken to transmit and receive the medical image is long depending on a kind of image and a communication environment, and therefore there is a case where it takes long time to display, on a client terminal, a medical image that has been subjected to image processing.

SUMMARY

In order to solve the above-described problem, an object of the present invention is to provide an image management device, an image display system, and an image display method, which are capable of shortening the time taken to display an image that has been subjected to image processing.

To achieve the abovementioned object, according to an aspect of the present invention, an image management device that is communicably connected to a client terminal and a plurality of image storage devices, reflecting one aspect of the present invention comprises:

a storage that stores identification information of image data with the identification information associated with an image storage device in which the image data is stored;

a hardware processor that identifies an image storage device that stores image data specified by an image-data transmission request received from the client terminal based on the identification information of the image data stored in the storage, and instructs the identified image storage device to subject the image data specified by the transmission request to image processing; and a communicator that receives, from the identified image storage device, processed image data that has been subjected to the image processing, and transmits the processed image data to the client terminal.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described in detail with reference to the drawings. However, the scope of the invention is not limited to the disclosed embodiments.

First of all, a configuration of an image display system according to the present embodiment will be described.

[Configuration of Image Display System]

Figure 1:
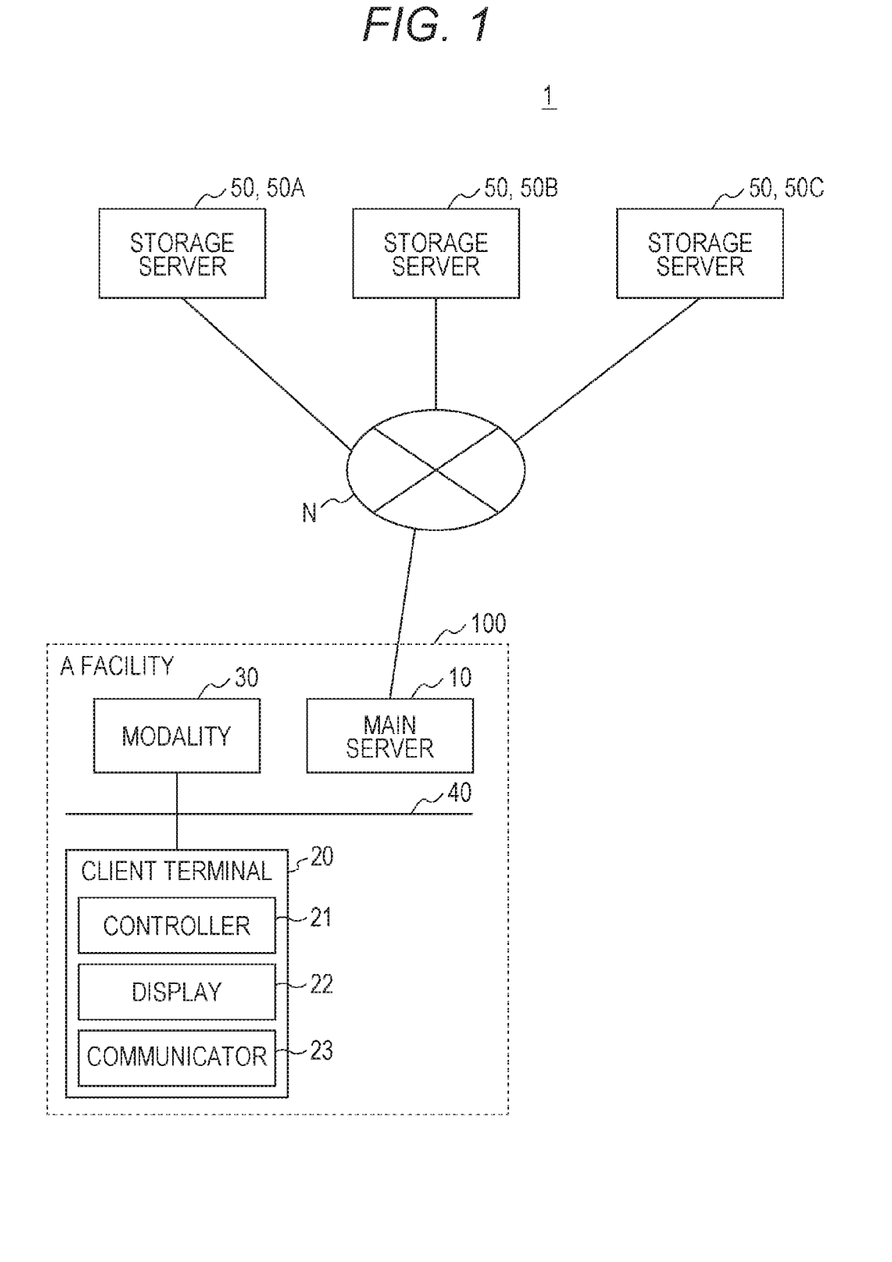
FIG. 1 is a diagram illustrating a schematic configuration of an image display system.

FIG. 1 is a diagram illustrating a schematic configuration of an image display system 1 according to the present embodiment.

As shown in FIG. 1, the image display system 1 includes an in-facility image display system 100 provided in a medical facility, and a plurality of storage servers (image storage devices) 50, and has a configuration in which the in-facility image display system 100 and the storage servers 50 are connected through a network N so as to enable data to be transmitted and received thereamong. The storage servers 50 may be cloud servers provided in a cloud environment.

The network N may be a LAN (Local Area Network) or a WAN (Wide Area Network), and may be configured to include a telephone network, an ISDN (Integrated Services Digital Network) network, a wideband communication network, an exclusive line, a mobile communication network, a communication satellite line, a CATV (Community Antenna Television) line, an optical communication line, a wireless communication line or the like, and an Internet service provider that provides a connection to the above-described network or line.

[Configuration of in-Facility Image Display System 100]

The in-facility image display system 100 is built in the medical facility, and has a configuration in which a main server (image management device) 10, a client terminal 20 and a modality 30 are connected through a communication network 40 such as a LAN (Local Area Network) so as to enable data to be transmitted and received thereamong.

In general, the DICOM (Digital Image and Communications in Medicine) standard is employed as a communication method used in the communication network 40. In the communication among devices that are connected through a LAN, DICOMMWM (Modality Worklist Management) and DICOMMPPS (Modality Performed Procedure Step) are used. It should be noted that communication methods that can be applied to the present embodiment are not limited to the above.

The main server 10 is, for example, a local server provided in a facility, and stores and manages medical information that has been transmitted from the client terminal 20, the modality 30 and the storage servers 50 through the communication network 40.

The medical information includes, for example, patient information about patients, inspection information about inspections, diagnostic information obtained by determining a kind, a medical condition and the like of an illness, image data (hereinafter referred to as "medical image data") of medical images generated by the modality 30, and supplementary information (image UID, inspection UID, Series UID, the date of imaging, patient identification information, a kind of modality, etc.) that accompanies the medical image data.

The main server 10 provides the medical information in response to a request from external devices such as the client terminal 20 and the storage servers 50.

The client terminal 20 includes: a controller 21 that includes a CPU (Central Processing Unit); a display 22 that is configured by a CRT (Cathode Ray Tube), an LCD (Liquid Crystal Display) or the like; a communicator (second communicator) 23 that controls communication with each device connected to the communication network 40; a storage that includes a HDD (Hard Disk Drive) and an RAM (Random Access Memory); an input that includes a keyboard and a mouse; and the like.

The client terminal 20 accesses the main server 10 through the communication network 40, and performs processing of reading, writing and the like of the medical information managed by the main server 10. For example, the client terminal 20 displays an electronic medical record on the basis of the patient information obtained from the main server 10, and displays a medical image on the display 22 on the basis of the medical image data obtained from the main server 10.

It should be noted that although FIG. 1 illustrates only one client terminal 20, the number thereof may be two or more.

The modality 30 images a diagnosis target region of a patient, and then digitally converts the imaged image to generate medical image data. The modality 30 is configured to include, for example, a CR (Computed Radiography), a CT (Computed Tomography), and an MRI (Magnetic Resonance Imaging). The modality 30 writes supplementary information to a header of medical image data in conformity with the DICOM standard, thereby causing the medical image data to be accompanied by the supplementary information.

Here, a configuration of the main server 10 will be described in detail.

Figure 2:
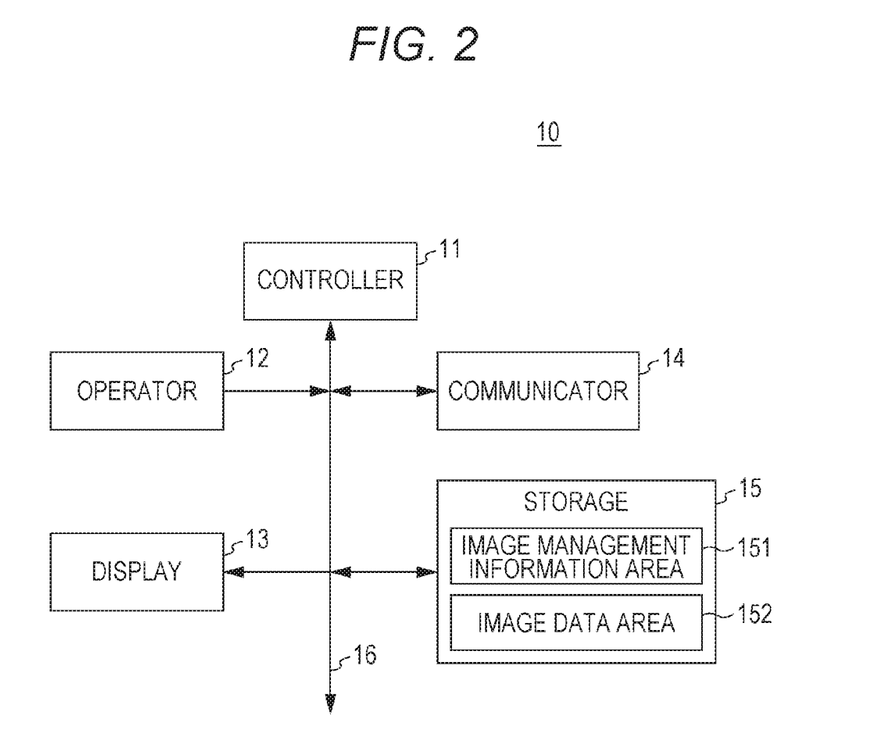
FIG. 2 is a block diagram illustrating, as an example, a functional configuration of a main server.

FIG. 2 is a diagram illustrating a functional configuration of the main server 10.

As shown in FIG. 2, the main server 10 includes, for example, a controller 11, an operator 12, a display 13, a communicator 14 and a storage 15. The above-described components are connected to one another through a bus 16.

The controller 11 includes a processor and a memory, for example, a CPU (Central Processing Unit), a ROM (Read Only Memory), and a RAM (Random Access Memory). The controller 11 controls the processing operation of each component of the main server 10 in a unified manner. The CPU reads various kinds of processing programs stored in the ROM to expand the programs in the RAM, and executes various kinds of processing according to the expanded programs.

The operator 12 includes a keyboard provided with a cursor key, a numeric input key and various kinds of function keys; and a pointing device such as a mouse. The operator 12 outputs, to the controller 11, an operation signal that has been input by the key operation made to the keyboard and the mouse operation.

The display 13 is configured by a LCD (Liquid Crystal Display), and displays various kinds of screens on the basis of display data input from the controller 11.

The communicator 14 is an interface for transmitting/receiving data to/from an external device such as the client terminal 20, the modality 30, and the storage server 50.

The storage 15 includes a HDD (Hard Disk Drive) and a semiconductor nonvolatile memory. The storage 15 stores data related to various kinds of processing.

More specifically, the storage 15 has an image management information area 151 and an image data area 152, and stores image management information and medical image data in the image management information area 151 and the image data area 152 respectively.

The image management information area 151 is an area for storing image management information that includes: supplementary information that is set in conjunction with generated medical image data; and information indicating a server in which the medical image data is stored. More specifically, a management table T1 is stored in the image management information area 151.

Figure 3:
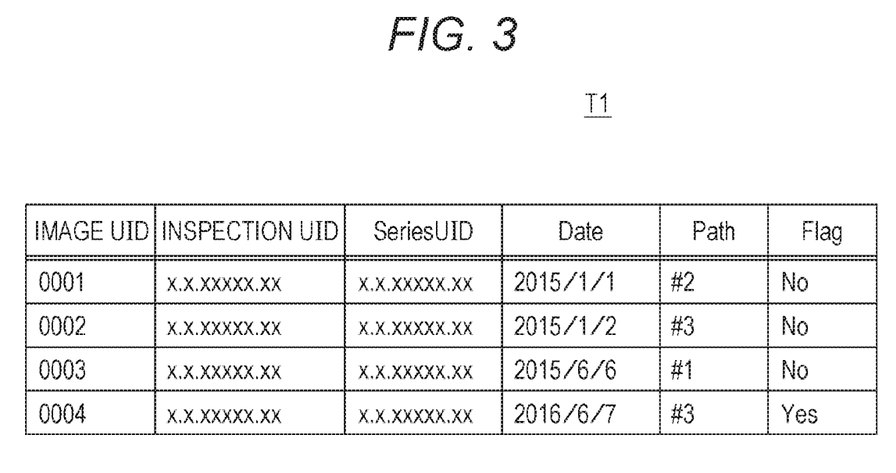
FIG. 3 is a chart illustrating an example of an image information table stored in the main server.

FIG. 3 shows an example of the management table T1.

As shown in FIG. 3, the management table T1 is composed of records, each of which has fields of supplementary information (image UID (identification information of image data), inspection UID, Series UID and the date), Path, and Flag on a medical image data basis.

Here, Path is information indicating a storage server to which the medical image data is transmitted (in which the medical image data is stored). It should be noted that the storage server to which the medical image data is transmitted (in which the medical image data is stored) is determined beforehand according to a kind of medical image data (for example, a kind of inspection, a kind of illness, a patient name, etc.).

Flag is information indicating whether or not the medical image data remains in the main server 10, that is to say, in the image data area 152 of the main server 10. A state in which the medical image data is stored in the image data area 152 is "Yes", whereas a state in which the medical image data is not stored in the image data area 152 is "No".

Medical image data, and a UID (image UID) of the medical image data, are stored in the image data area 152 with the medical image data associated with the UID (image UID). The medical image data is configured to be deleted when a predetermined time period has passed after the medical image data is stored (for example, after the lapse of half a year from the generation of an image, or after the completion of medical treatment).

[Configuration of Storage Server 50]

Next, a configuration of each of the storage servers 50 will be described in detail.

Figure 4:
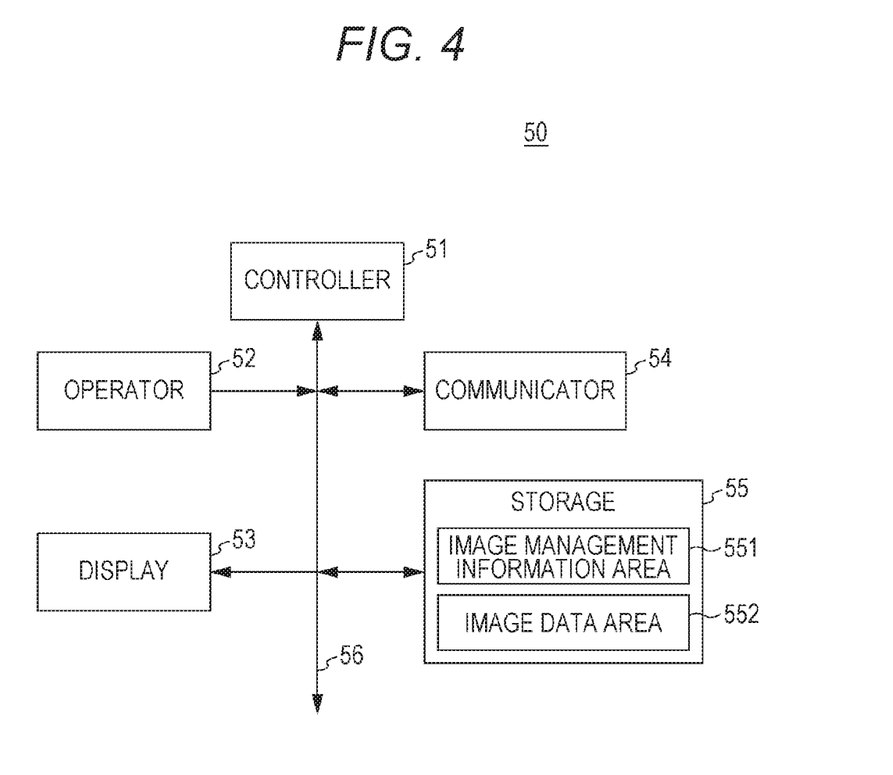
FIG. 4 is a block diagram illustrating, as an example, a functional configuration of a storage server.

FIG. 4 shows a functional configuration of each of the storage servers 50.

As shown in FIG. 4, the storage servers 50 includes, for example, a controller 51 as an image processor, an operator 52, a display 53, a communicator 54 as a return part, and a storage 55. The above-described components are connected to one another through a bus 56.

The controller 51 includes a CPU, a ROM and a RAM, and controls the processing operation of each component of the storage server 50 in a unified manner. The CPU reads various kinds of processing programs stored in the ROM to expand the programs in the RAM, and executes various kinds of processing according to the expanded programs.

The operator 52 includes a keyboard provided with a cursor key, a numeric input key and various kinds of function keys; and a pointing device such as a mouse. The operator 12 outputs, to the controller 51, an operation signal that has been input by the key operation made to the keyboard and the mouse operation.

The display 53 is configured by a LCD, and displays various kinds of screens on the basis of display data input from the controller 51.

The communicator 54 is an interface for transmitting/receiving data to/from an external device such as the main server 10, and the other storage servers 50.

The storage 55 includes a HDD and a semiconductor nonvolatile memory. The storage 55 stores data related to various kinds of processing.

More specifically, the storage 55 has an image management information area 551 and an image data area 552, and stores image management information and medical image data in the image management information area 551 and the image data area 552 respectively.

The image management information area 551 and the image data area 552 are configured in the same manner as the image management information area 151 and the image data area 152 of the main server 10 respectively.

Here, all of the storage servers 50 share the same management table T1 stored in the image management information area 551. In addition, the management table T1 stored in each of the storage servers 50 is also the same as the management table T1 stored in the image management information area 151 of the main server 10. In other words, the main server 10 and all of the storage servers 50 each store the same management table T1.

Meanwhile, the medical image data is stored only in the image data area 552 of a predetermined storage server 50.

In other words, in the storage 55, when the image management information and the medical image data are transmitted from the main server 10, the image management information and the medical image data are stored in the image management information area 151 and the image data area 552 respectively.

Moreover, when only the image management information is transmitted from the main server 10, the information is stored in the image management information area 551.

For example, when the management table T1 shown in FIG. 3 is stored in the image management information area 551, the storage server 50A (NO. 1) stores medical image data of "image UID: 0003" in the image data area 552.

In addition, the storage server 50B (NO. 2) stores medical image data of "image UID: 0001" in the image data area 552.

Moreover, the storage server 50C (NO. 3) stores medical image data of "image UID: 0002" and "image UID 0004" in the image data area 552.

Next, the operation of the image display system 1 according to the present embodiment will be described.

[Update Processing of Management Table T1]

In the image display system 1, medical image data generated by the modality 30 is transmitted to the main server 10. The main server 10 manages the received medical image data on the basis of image management information of the management table T1. When the main server 10 receives the medical image data, the main server 10 updates the management table T1. It should be noted that the medical image data is transmitted to any one of the storage servers 50 which is determined according to a kind of the medical image data (for example, a kind of inspection, a kind of illness, a patient name, etc.). In addition, the image management information stored in the management table T1 is configured to be shared by all of the storage servers 50.

Figure 5:
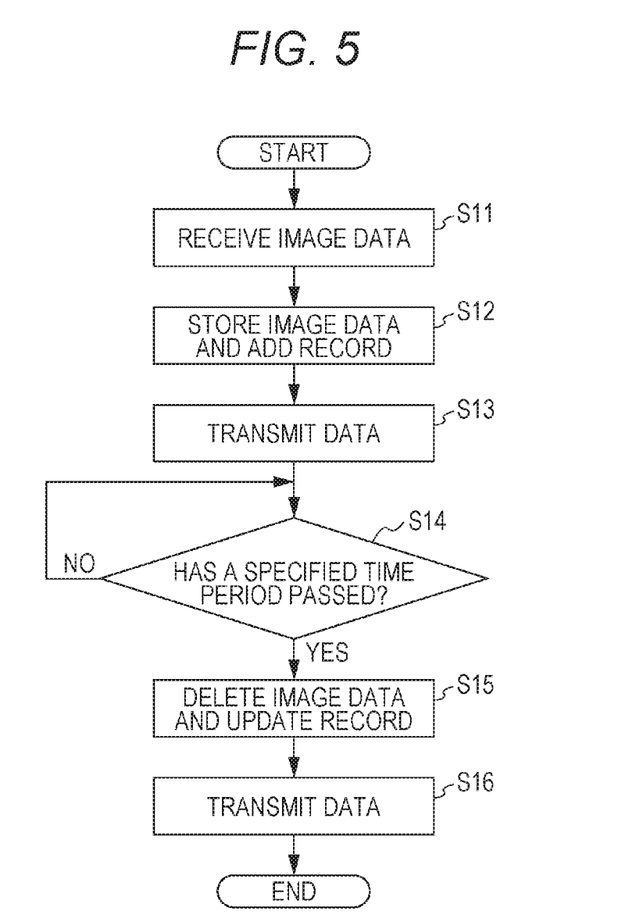
FIG. 5 is a flowchart illustrating database update processing.

FIG. 5 is a flowchart illustrating update processing of updating the management table T1 of the main server 10.

Figure 6A:
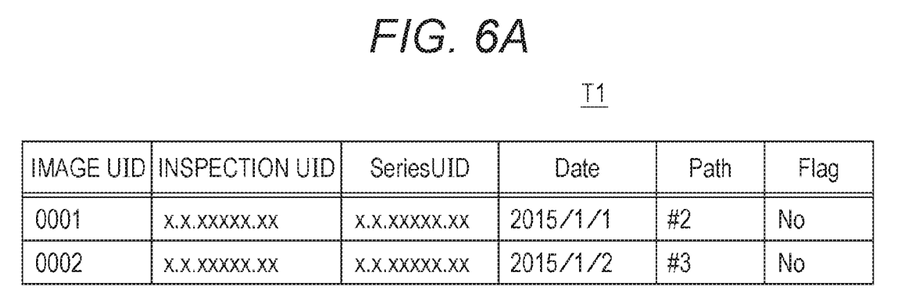
FIGS. 6A to 6C are tables each illustrating updating of a database.

Here, it is assumed that the main server 10 stores the management table T1 having two records, as shown in FIG. 6A, in the image management information area 151 of the storage 15.

First of all, when the controller 11 receives medical image data from the modality 30 (step S11), the controller 11 stores the medical image data in the image data area 152, adds a record to the management table T1 in the image management information area 151 (step S12), transmits image management information and the medical image data to one of the storage servers 50, and transmits the image management information to the other storage servers 50 (step S13).

Here, the one of the storage servers 50, to which the medical image data is transmitted, is determined according to a kind of the medical image data (for example, a kind of inspection, a kind of illness, a patient name, etc.).

Figure 6B:
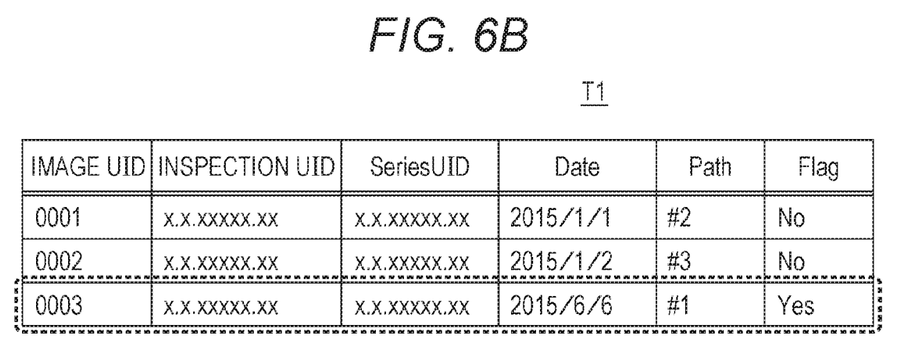

FIG. 6B shows, as an example, a state in which a new record of "image UID: 0003" is added to the management table T1.

The example of FIG. 6B shows that medical image data of "image UID: 0003" is transmitted to the storage server 50A (NO. 1).

In other words, in the example of FIG. 6B, the controller 11 transmits the image management information and the medical image data to the storage server 50A, and transmits only the image management information to the storage servers 50B, 50C.

Next, the controller 11 determines whether or not a predetermined time period has passed (step S14). When it is determined that the predetermined time period has not passed (step S14: No), the controller 11 repeats processing of the step S14.

Meanwhile, when it is determined that the predetermined time period has passed (step S14: Yes), the controller 11 deletes the medical image data stored in the image data area 152, and updates the record (step S15).

Figure 6C:
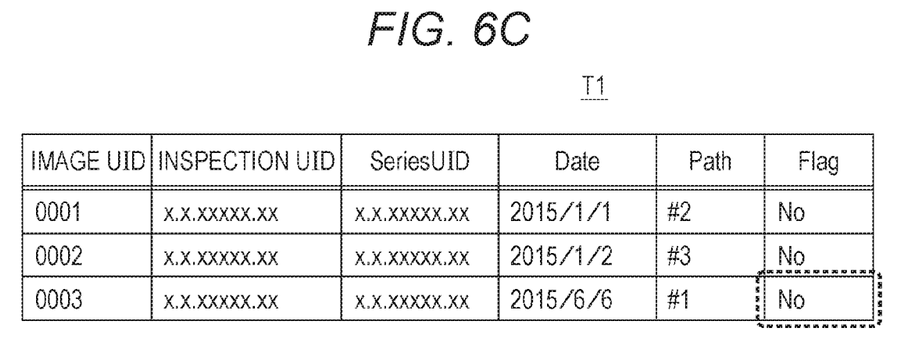

FIG. 6C shows, as an example, a state in which when the medical image data has been deleted, the record has been updated. In the example of FIG. 6C, the medical image data of "image UID: 0003" has been deleted, and therefore "Flag" is updated from "Yes" to "No" in the record of "image UID: 0003".

Next, the controller 11 transmits, to all of the storage servers 50, information indicating that the medical image data of "image UID: 0003" has been deleted (step S13). The controller 11 then ends the present processing. As the result, the image management information stored in the management table T1 is configured to be shared by all of the storage servers 50.

[Image Display Processing]

Next, image display processing of displaying a medical image on the client terminal 20 in the image display system 1 will be described.

In the image display system 1 according to the present embodiment, when a medical image is displayed on the client terminal 20, a device (the main server 10 or the storage server 50) that stores medical image data subjects the medical image data to image processing, and then provides the client terminal 20 with the medical image data that has been subjected to the image processing.

Figure 7:
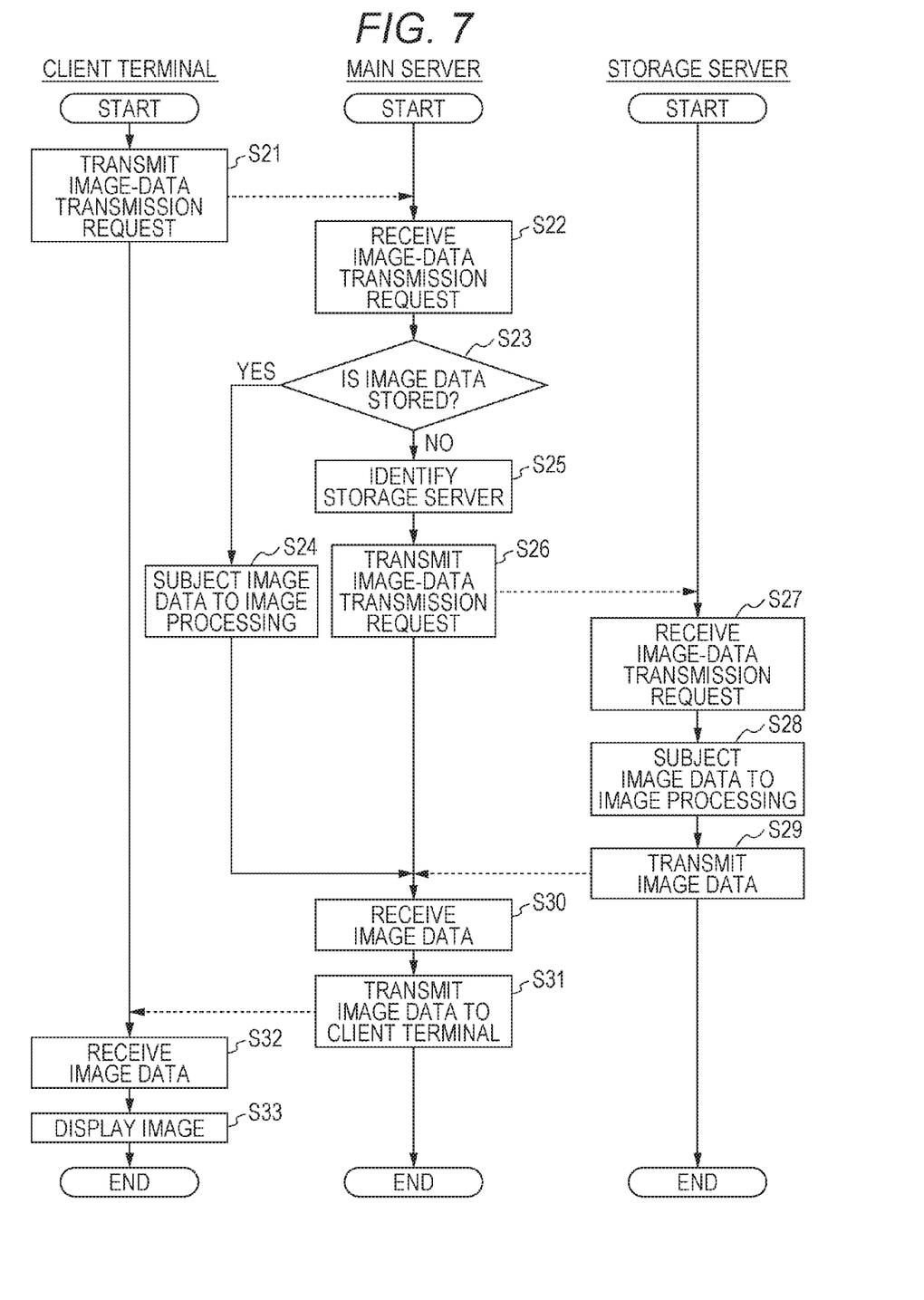
FIG. 7 is a flowchart illustrating image display processing.

FIG. 7 is a flowchart illustrating image display processing. Here, it is assumed that the main server 10 stores the management table T1 shown in FIG. 6B.

First of all, the controller 21 of the client terminal 20 requests the main server 10 to transmit medical image data of a predetermined image (step S21).

Next, when the controller 11 of the main server 10 receives, from the client terminal 20, the transmission request to transmit the medical image data (step S22), the controller 11 determines whether or not the medical image data specified by the transmission request is stored in the image data area 152 (step S23).

Subsequently, when it is determined that the medical image data is stored (step S23: Yes), the controller 11 subjects the medical image data to predetermined image processing (for example, image generation processing for radiogram interpretation, analytical processing, etc.) (step S24), and the process then proceeds to the undermentioned step S30.

This corresponds to a case where a transmission request to transmit medical image data of "image UID: 0003" is received from the client terminal 20 in the example of FIG. 6B.

Meanwhile, when it is determined that the medical image data is not stored (step S23: No), the controller 11 refers to "Path" in the management table T1 to identify the storage server 50 that stores the medical image data (step S25), and subsequently requests the storage server 50 to subject the medical image data to image processing, and then to transmit the medical image data (step S26).

In the example of FIG. 6B, when a transmission request to transmit medical image data of "image UID: 0001" is received from the client terminal 20, the controller 11 instructs the storage server 50B (NO. 2).

In addition, when a transmission request to transmit medical image data of "image UID: 0002" is received from the client terminal 20, the controller 11 instructs the storage server 50C (NO. 3).

Next, when the controller 51 of the storage server 50 receives a transmission request to transmit medical image data (step S27), the controller 51 subjects specified medical image data to predetermined image processing (for example, image generation processing for radiogram interpretation, analytical processing, etc.) (step S28), and transmits, to the main server 10, the medical image data that has been subjected to the image processing (step S29).

Subsequently, the controller 11 of the main server 10 receives the medical image data that has been subjected to the image processing, and that has been transmitted from the storage server 50 (step S30), and then transmits the medical image data to the client terminal 20 (step S31).

After that, the controller of the client terminal 20 receives, from the storage server 50, the medical image data that has been subjected to the image processing (step S32), instructs the display 22 to display an image based on the medical image data (step S33), and then ends the present processing.

Incidentally, for example, in a case where two images are displayed side by side in the client terminal 20, and when a transmission request to transmit medical image data corresponding to the two images is transmitted from the client terminal 20, the main server 10 refers to "Flag" in each record related to medical image data in the management table T1 to determine whether or not the medical image data is stored. Image processing is performed in the main server 10 or the storage server 50 as described above, and two pieces of medical image data are then transmitted to the client terminal 20.

For example, when a transmission request to transmit medical image data of "image UID: 0002" and "image UID: 0003" in FIG. 6B is received, the main server 10 instructs the storage server 50C to subject the medical image data of "image UID: 0002" to image processing, and subjects the medical image data of "image UID: 0003" to image processing by the own device.

As described above, according to the present embodiment, there is provided the main server 10 that is communicably connected to the client terminal 20 and the plurality of storage servers 50, the main server 10 being provided with: the storage 15 that stores identification information of image data with the identification information associated with the storage server 50 in which the image data is stored; the controller 11 that, when a transmission request to transmit image data is received from the client terminal 20, identifies, on the basis of identification information of the image data stored in the storage 15, the storage server 50 that stores image data specified by the transmission request, and then instructs the identified storage server 50 to subject the image data specified by the transmission request to image processing; and the communicator 14 that obtains, from the identified storage server 50, processed image data that has been subjected to the image processing, and transmits the processed image data to the client terminal 20.

Accordingly, medical image data is subjected to image processing in a server that stores the medical image data, and the medical image data that has been subjected to the image processing is transmitted to the client terminal 20. Therefore, transfer of medical image data between servers can be suppressed to the minimum, and the time taken from the image processing until displaying can be shortened.

In addition, according to the present embodiment, the storage 15 stores image data and identification information thereof with the image data associated with the identification information, the controller 11 deletes image data after the lapse of a predetermined time period after the image data is stored in the storage 15, and when image data specified by the transmission request does not exist in the storage 15, the controller 11 identifies the storage server 50 that stores the image data.

Accordingly, when medical image data exists in the main server 10, image processing is performed in the main server 10, and therefore the number of times medical image data is transmitted can be further suppressed, which enables to shorten the time taken from the image processing until displaying.

Incidentally, in the above-described embodiment, when medical image data is not stored in the storage 15, the controller 11 of the main server 10 identifies the storage server 50 that stores the image data, and transmits an instruction to the storage server 50 as described above. However, the image display system 1 may be configured in such a manner that when a load of image processing is higher than a predetermined value, the controller 11 identifies the storage server 50 that stores the image data, and transmits an instruction to the storage server 50.

The load of image processing can be determined by, for example, an operating rate of the CPU, or memory utilization.

In other words, when it is determined that a load placed on the own device is higher than a predetermined value, the controller 11 of the main server 10 identifies the storage server 50 that stores the medical image data, and transmits an instruction to the storage server 50.

Moreover, the image display system 1 may be configured in such a manner that according to a kind of image processing to which the medical image data is subjected, in other words, for example, when a load of processing is high, the main server 10 identifies the storage server 50 that stores the medical image data, and transmits an instruction to the storage server 50.

As the result of configuring the image display system 1 in this manner, when it is determined that a load placed on the main server 10 is high, image processing is performed in the storage server 50, and therefore the time taken to complete the image processing can be shortened, which enables to shorten the time taken from the image processing until displaying.

Further, the medical image data in the above-described embodiment may include not only still image data but also moving image data.

In this case as well, when a transmission request to transmit moving image data is transmitted from the client terminal 20 to the main server 10, the main server 10 or the storage server 50, which stores the moving image data, subjects the moving image data to predetermined image processing, and then transmits the moving image data to the client terminal 20.

Furthermore, the above-described embodiment presents a configuration in which the storage servers 50 are connected to only one facility A. However, the storage servers 50 may be connected to other facilities.

For example, the following configuration may be employed: the storage servers 50A, 50B are connected to only the facility A; and the storage server 50C is connected to the facility A and other facilities so as to be shared thereamong.

As the result of employing the above configuration, image management information of medical image data generated in the aforementioned other facilities is also stored in the management table T1 because the main server 10 and all of the storage servers 50 share the same management table T1. Therefore, the aforementioned facilities are also allowed to browse, for example, medical images of the same patient.

Although embodiments of the present invention have been described and illustrated in detail, it is clearly understood that the same is by way of illustration and example only and not limitation, the scope of the present invention should be interpreted by terms of the appended claims.

What is claimed is:

1. An image management device that is communicably connected to a client terminal and a plurality of image storage devices, the image management device comprising:
    a storage that stores identification information of image data with the identification information associated with an image storage device in which the image data is stored;
    a hardware processor that identifies an image storage device that stores image data specified by an image-data transmission request received from the client terminal based on the identification information of the image data stored in the storage, and instructs the identified image storage device to subject the image data specified by the transmission request to image processing; and
    a communicator that receives, from the identified image storage device, processed image data that has been subjected to the image processing, and transmits the processed image data to the client terminal;
    wherein the instruction by the hardware processor to subject the image data specified by the transmission request to image processing is a post-transferring process that instructs a source how an image is to be processed prior to transfer so that a destination can correctly handle the image upon arrival;
    wherein the image storage device is a storage server of a plurality of storage servers, the plurality of storage servers connected to the client terminal via the image management device; and
    wherein the image processing occurs at one of a storage server of the plurality of storage servers or the image management device prior to transmission of the image to the destination.

2. The image management device according to claim 1, wherein
    the storage stores image data and identification information thereof with the identification information associated with the image data,
    the hardware processor deletes image data after the lapse of a predetermined time period after the image data is stored in the storage,
    the hardware processor determines whether or not image data specified by the transmission request received from the client terminal exists in the storage, and
    when it is determined that the image data specified by the transmission request does not exist in the storage, the hardware processor identifies an image storage device that stores the image data.

3. The image management device according to claim 1, wherein
    the hardware processor calculates a value of a load placed on the hardware processor when the transmission request is received from the client terminal, and
    the hardware processor identifies an image storage device that stores image data specified by the transmission request when it is determined that the calculated load is higher than a predetermined value.

4. The image management device according to claim 3, wherein
    the hardware processor includes a processor and a memory, and calculates a value of a load placed on the hardware process on the basis of an operating rate of the processor or memory utilization of the memory.

5. The image management device according to claim 1, wherein
    image data includes moving image data.

6. An image display system comprising:
    an image management device;
    a client terminal that is communicably connected to the image management device; and
    a plurality of image storage devices that are communicably connected to the image management device, wherein the image management device comprises:

a storage that stores identification information of image data with the identification information associated with an image storage device in which the image data is stored;

a hardware processor that identifies an image storage device that stores image data specified by an image-data transmission request received from the client terminal based on the identification information of the image data stored in the storage, and instructs the identified image storage device to subject the image data specified by the transmission request to image processing; and a communicator that receives, from the identified image storage device, processed image data that has been subjected to the image processing, and transmits the processed image data to the client terminal; and wherein wherein the instruction by the hardware processor to subject the image data specified by the transmission request to image processing is a post-transferring process that instructs a source how an image is to be processed prior to transfer so that a destination can correctly handle the image upon arrival;

the plurality of image storage devices are each provided with an image processor that subjects image data specified by the transmission request to image processing according to an instruction from the image management device, and a return part that returns, to the image management device, processed image data that has been subjected to image processing by the image processor, and the client terminal includes a second communicator that transmits the transmission request to the image management device, and receives processed image data from the image management device, and a display that displays an image on the basis of the received processed image data;

wherein the image storage device is a storage server of a plurality of storage servers, the plurality of storage servers connected to the client terminal via the image management device; and wherein the image processing occurs at one of a storage server of the plurality of storage servers or the image management device prior to transmission of the image to the destination.

7. An image display method used in an image display system including:

an image management device that is communicably connected to a client terminal, and has a storage that stores identification information of image data with the identification information associated with an image storage device in which the image data is stored; and a plurality of image storage devices that are communicably connected to the image management device, the image display method comprising:

in the image management device, when an image-data transmission request is received from the client terminal, identifying an image storage device that stores image data specified by the transmission request on the basis of the identification information of the image data stored in the storage, and instructing the identified image storage device to subject the image data specified by the transmission request to image processing;

in the identified image storage device, subjecting image data specified by the transmission request to image processing according to the instruction in the instructing; and in the client terminal, causing a display to display an image on the basis of processed image data that has been subjected to the image processing by the image processing;

wherein the instructing the identified image storage device to subject the image data specified by the transmission request to image processing is a post-transferring process that instructs a source how an image is to be processed prior to transfer so that a destination can correctly handle the image upon arrival;

wherein the image storage device is a storage server of a plurality of storage servers, the plurality of storage servers connected to the client terminal via the image management device; and wherein the image processing occurs at one of a storage server of the plurality of storage servers or the image management device prior to transmission of the image to the destination.

* * * * *